United States Patent [19]

Murtha et al.

[11] 4,434,082

[45] Feb. 28, 1984

[54] PALLADIUM/HETEROPOLYACID/SURFACTANT CATALYST SYSTEM

[75] Inventors: Timothy P. Murtha; Tad K. Shioyama, both of Bartlesville, Okla.

[73] Assignee: Phillips Petroleum Company, Bartlesville, Okla.

[21] Appl. No.: 367,825

[22] Filed: Apr. 12, 1982

[51] Int. Cl.$^3$ .............................................. B01J 31/02
[52] U.S. Cl. .................................. 502/164; 568/401; 502/168; 502/169
[58] Field of Search ................... 252/429 R, 437, 430; 568/401

[56] References Cited

U.S. PATENT DOCUMENTS

| 3,379,651 | 4/1968 | Hargis et al. | 252/437 |
| 4,152,354 | 5/1979 | Stapp | 260/597 B |
| 4,203,927 | 5/1980 | Stapp | 568/401 |
| 4,386,217 | 5/1983 | Anbinder et al. | 252/429 R |

FOREIGN PATENT DOCUMENTS 1508331  3/1975  United Kingdom.

*Primary Examiner*—W. J. Shine

[57] ABSTRACT

A Pd/heteropolyacid/surfactant catalyst system, when used with proper diluents, improves the oxidation of olefins to ketones, while reducing corrosive effects.

9 Claims, No Drawings

PALLADIUM/HETEROPOLYACID/SURFACTANT CATALYST SYSTEM

BACKGROUND OF THE INVENTION

The Wacker-type oxidation of ethylene to acetaldehyde using a palladium chloride/cupric chloride/hydrochloric acid catalyst in an aqueous solution has been modified and applied to the synthesis of methyl ketones from terminal olefins. However, major problems have been encountered in using the Wacker-type oxidation in the oxidation of higher olefins and internal olefins. One problem is that of reduced rates of reaction due to the low solubility of the olefin in the aqueous medium. Another major problem is the concomitant secondary oxidation of the ketone product which leads to poor selectivities and poor yield of desired product.

The solubility problems encountered in the Wacker-type oxidation of higher olefins have been at least partially solved by resorting to "phase transfer" techniques and the addition of a suitable surfactant. Thus, the prior art teaches that the reaction of the olefinic hydrocarbon reactant to be oxidized in the presence of free oxygen is preferably carried out in a multi-phase diluent system, preferably a two-phase system with one phase aqueous and the other organic. The catalysts known for this multi-phase process are Pd/Cu/alkali metal or alkaline earth metal chloride catalyst or Pd/Cu/boric acid catalyst with the palladium being either free palladium or a palladium compound and the copper component being either a cuprous or a cupric compound. It should also be noted that the HCl used in conventional Wacker oxidation reactions to maintain adequate conversion levels of the olefinic reactant has been eliminated as a component of the multi-phase process. An additional component of this multi-phase prior art reaction system is a suitable surfactant.

Corrosion of metallic process equipment is an additional problem when a catalyst containing halide ions such as the conventional Wacker or modified Wacker-type catalysts are utilized in the oxidation process, and a low-corrosion catalyst can be desirable at times.

THE INVENTION

In accordance with the present invention, an oxidation process is described wherein a catalyst with greatly reduced halide content is utilized in a multi-phase diluent system with the addition of a suitable surfactant. In one embodiment of the invention, a catalyst system containing $PdCl_2$, a prepared heteropolyacid $H_9[PMo_6V_6O_{40}]$, cetyltrimethylammonium bromide as phase transfer catalyst, and water and decane as a two-phase diluent system show good results in the oxidation of 2-butene to methyl ethyl ketone.

The concentration of chloride ion has been reduced by a factor of 6 from a previous catalyst system containing cupric chloride and boric acid along with palladium chloride and a phase transfer catalyst. Thus, the use of less expensive reactors would be possible for the oxidation of olefins because corrosion problems would not be sever.

ADVANTAGES

In addition to the reduction in halide concentration, with resultant lowering of corrosion effects and production costs, the invention has other advantages.

The production of chlorinated by-products, such as the 3-chloro-2-butanone produced in the oxidation of 1-butene or 2-butene, is reduced or eliminated. This means that catalyst reactivity/selectivity is high and by-product removal operations are simplified, resulting in lower costs.

OBJECTS OF THE INVENTION

It is one object of the invention to produce a catalyst useful for the oxidation of olefins to ketones.

It is another object of the invention to produce a process whereby ketones can be efficiently produced via the oxidation of olefins.

DESCRIPTION OF THE INVENTION

I. Catalyst System

The catalyst utilized according to the instant invention for the oxidation of olefinic hydrocarbons to carbonyl compounds is made up of three components: (1) a palladium component, (2) a heteropolyacid component, and (3) a surfactant component.

(1) Palladium Component

The palladium component of the catalyst system of the instant invention can be any palladium-containing material whose properties render it suitable for use in Wacker or Wacker-type reactions. The palladium component of the invention can be palladium metal, e.g., finely divided palladium powder, or a palladium compound. Examples of suitable palladium compounds include allyl palladium chloride dimer $[C_3H_5PdCl]_2$, dichlorobis(triphenylphosphine)palladium(II), palladium(II) acetate, palladium(II) acetylacetonate, tetrakis(triphenylphosphine)palladium(O), palladium(II) chloride, palladium(II) iodide, palladium(II) nitrate, palladium(II) sulfate, and the like. Mixtures of the above palladium compounds can also be utilized as the palladium component of the instant catalyst system if so desired, thus providing a means to minimize the halide content of the catalyst system.

(2) Heteropolyacid Component

The heteropolyacid component of the catalyst system of the instant invention should have a redox potential in excess of 0.5 volt and contain at least two metallic species. It is preferred that it contain molybdenum and vanadium. Such preferred heteropolyacids are defined herein as iso-polymolybdates in which one or more of the molybdenum atoms are replaced by vanadium or an iso-polyvanadate in which one or more of the vanadium atoms are replaced by molybdenum.

The polyacid used contains vanadium atoms, for example from 1 to 8, more preferably 6 atoms, in a molecule, and molybdenum. Typical polyacids for use in the present invention are represented by the following general formula:

$$H_m[X_xMo_aV_bM_yO_z]$$

in which

X is B, Si, Ge, P, As, Se, Te or I;

M is W, Nb, Ta or Re;

m, a, b and z are integers;

x is zero (for mixed isopolyacids) or an integer (for hetero-polyacids);

and y is zero or an integer such that $$6 \leq \frac{y+a+b}{z} \leq 12$$

and $$m+Nx+6a+5b+N'y \leq 2z$$

in which each of N and N' is the number of the group of the periodic table to which X and M respectively belong. Examples of typical heteropolyacids are as follows:

| Heteropolyacid | Redox potential, V |
|---|---|
| $H_9[TeMo_3V_3O_{24}]$ | +0.80 |
| $H_4[As_2Mo_{12}V_6O_{61}]$ | +0.65 |
| $H_3[AsMo_6V_6O_{40}]$ | +0.72 |
| $H_6[SiMo_{10}V_2O_{40}]$ | |
| $H_6[GeMo_{10}V_2O_{40}]$ | |
| $H_n[PMo_pV_qO_{40}]$*, for example: | |
| $H_4[PMo_{11}VO_{40}]$ | +0.65 |
| $H_5[PMo_{10}V_2O_{40}]$ | +0.70 |
| $H_6[PMo_9V_3O_{40}]$ | +0.72 |
| $H_7[PMo_8V_4O_{40}]$ | +0.75 |
| $H_8[PMo_7V_5O_{40}]$ | +0.76 |
| $H_9[PMo_6V_6O_{40}]$ | +0.77 |
| $H_{10}[PMo_5V_7O_{40}]$ | +0.79 |
| $H_{11}[PMo_4V_8O_{40}]$ | +0.80 |
| $H_5[Mo_rW_mV_2O_{40}]$** | |
| $H_9[PMo_3W_3V_6O_{40}]$ | +0.70 |

*in which n = 3 + q, p = 12 − q, q = 1 to 10
**in which m = 2, 4, 6, or 8 and r = 10 − m.

The ratios of the various catalyst components can be expressed in terms of a molar ratio of heteropolyacid to palladium. The molar ratio of heteropolyacid component to palladium component in the instant catalyst system is broadly up to 50/1.

The amount of catalyst employed according to the instant invention can be expressed in terms of the molar ratio of olefinic hydrocarbon reactant to palladium component of the catalyst system. Broadly, the molar ratio of olefinic reactant to palladium component is from about 5/1 up to 1000/1 and preferably from about 10/1 up to 250/1.

(3) Surfactant Component

Generally, the surfactant component of the reaction system according to the instant invention comprises one or more compounds which exhibit surface-active properties—i.e., surfactants. However, the term "surfactant" encompasses a very broad class of compounds, and it has been discovered that not all surfactants are suitable for use in the instant invention. Nevertheless, for convenience and simplicity, the suitable compounds that can be employed according to the instant invention and described more fully below will be termed surfactants herein. At the present time, it is not known whether, in the catalyst and process of the invention, these compounds function as phase-transfer catalysts, such as is taught in the art, or whether they function as micellar catalysts, a feature also disclosed in the prior art. Because of this uncertainty in the mode of action of these compounds in the instant invention and for convenience, the following compounds will merely be described herein as surfactants.

A preferred surfactant for use in the reaction system of the instant invention is selected from one of the five following groups:

(A) Quaternary ammonium salts of the general formula $(R''')_4N^+X^-$ wherein $R'''$ is an alkyl radical of from 1 to 20 carbon atoms and wherein the total number of carbon atoms in said quaternary ammonium salt is from 8 to 30 carbon atoms broadly and preferably from 16 to 22 carbon atoms; and wherein X is selected from the group consisting of $Br^-$, $Cl^-$, $I^-$, $F^-$, $R'''CO_2^-$, $QSO_3^-$, $BF_4^-$, and $HSO_4^-$, wherein Q is an aryl, alkaryl or arylalkyl radical of 6 to 10 carbon atoms. It will be noted that a variety of anions are suitable as the $X^-$ component of the quaternary ammonium salts.

Useful quaternary ammonium salts according to the general formula given above include cetyltrimethylammonium bromide, hexadecyltrimethylammonium bromide, tetraheptylammonium bromide, cetyltrimethylammonium stearate, benzyltributylammonium chloride, benzyltriethylammonium bromide, benzyltrimethylammonium bromide, phenyltrimethylammonium bromide, phenyltrimethylammonium iodide, tetrabutylammonium bromide, tetrabutylammonium chloride, tetrabutylammonium hydrogen sulfate, tetrabutylammonium iodide, tetraethylammonium bromide, tetrabutyl ammonium fluoride, and tetrabutylammonium tetrafluoroborate.

(B) Alkali metal alkyl sulfates of the general formula $R'^\nu OSO_3M$, wherein $R'^\nu$ is an alkyl radical having from 10 to about 20 carbon atoms and wherein M is an alkali metal. Examples of suitable compounds according to the general formula for the alkali metal alkyl sulfates include lithium decylsulfate, potassium dodecylsulfate, sodium dodecylsulfate, sodium hexadecylsulfate, potassium hexadecylsulfate, rubidium dodecylsulfate, cesium dodecylsulfate, sodium octadecylsulfate, potassium octadecylsulfate, potassium eicosylsulfate, sodium eicosylsulfate and the like.

(C) Alkali metal salts of alkanoic acids of the general formula $R'^\nu CO_2M$, wherein $R'^\nu$ and M have the same meaning as given above for the compounds of (B). Examples of suitable alkali metal salts of alkanoic acids include lithium decanoate, sodium dodecanoate, potassium dodecanoate, rubidium dodecanoate, cesium dodecanoate, sodium hexadecanoate, potassium hexadecanoate, sodium octadecanoate, potassium octadecanoate, sodium eicosenoate, potassium eicosenoate, and the like.

(D) Alkali metal salts of alkaryl sulfonic acids of the general formula

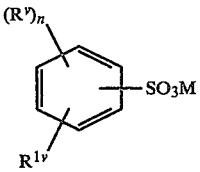

wherein $R'^\nu$ and M have the same meaning as given and wherein $R^{1\nu}$ is an alkyl radical of 1 to 4 carbon atoms and wherein n is 0 or an integer of from 1 to 4. Typical compounds within the (D) group include sodium dodecylbenzenesulfonate, potassium dodecylbenzenesulfonate, lithium dodecylbenzenesulfonate, sodium tetradecylbenzenesulfonate, potassium hexadecylbenzenesulfonate, rubidium dodecylbenzenesulfonate, cesium dodecylbenzenesulfonate, sodium octadecylbenzenesulfonate, potassium octadecylbenzenesulfonate, sodium eicosylbenzenesulfonate, potassium dodecyltoluenesulfonate, sodium dodecylxylenesulfonate and the like.

(E) 1-Alkyl pyridinium salts of the general formula

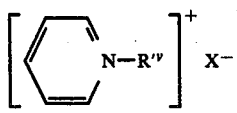

wherein R'" and X⁻ have the same meanings as described above. Examples of suitable 1-alkyl pyridinium salts are 1-dodecylpyridinium para-toluenesulfonate, 1-dodecylpyridinium chloride, 1-hexadecylpyridinium chloride, 1-hexadecylpyridinium para-toluenesulfonate, 1-decylpyridinium chloride, 1-hexadecylpyridinium bromide, 1-tetradecylpyridinium chloride, 1-octadecylpyridinium chloride, 1-eicosylpyridinium chloride, 1-octadecylpyridinium benzenesulfonate, and the like.

The amount of surfactant compound selected from groups (A) through (E) which is utilized according to the instant invention can be expressed in terms of a mole ratio based on the palladium component of the catalyst system. Broadly, the mole ratio of surfactant to palladium compound will be from 0.01/1 to 10/1. Preferably, it will be from 0.1/1 to 3/1.

II. Diluent System

As indicated above, the oxidation of the olefinic hydrocarbon according to the instant invention is carried out in the presence of a diluent comprised of at least two liquid phases, preferably only two, at least one of which is an aqueous phase.

The nonaqueous phase will hereinafter be termed the organic phase. Said organic phase should be relatively inert to the oxidation conditions, of course, and also relatively inert to hydrolysis-type reactions. Furthermore, it is apparent that if at least two phases are present, at least one of which is an aqueous phase, that the organic diluent utilized must have somewhat limited solubility in the aqueous phase. In addition, the choice of the organic diluent(s) may be often determined based on the difference in boiling points expected between the product of the oxidation reaction and the organic diluent so as to facilitate separation of the components of the reaction mixture. Within these general requirements, a rather broad range of organic compounds can be utilized to form the organic phase according to the instant invention.

Generally speaking, suitable compounds can be found in the classes of compounds described as aliphatic hydrocarbons, aromatic hydrocarbons or alkylsubstituted aromatic hydrocarbons, halogenated aromatic compounds, and esters of aromatic carboxylic acids although the latter may be less preferred because of a tendency toward hydrolysis of the ester group in certain instances. In addition, it has been found that compounds such as nitrobenzene and benzonitrile, commonly utilized as solvents for many organic reactions, show a definite inhibitory effect on the reaction of the instant invention presumably by complexing of one or more catalyst components.

Suitable organic diluents include cyclohexane, hexane, octane, decane, dodecane, tetradecane, hexadecane, benzene, toluene, chlorobenzene, methylbenzoate, bromobenzene, 1,2,4-trichlorobenzene, ortho-dichlorobenzene, sulfolane, ortho-xylene, para-xylene, meta-xylene, methylcyclopentane, dimethyl ortho-phthalate, and the like. Mixtures of organic diluents may be utilized in some cases as desired.

The amounts of the aqueous phase and organic diluent phase based on the starting olefinic reactant can vary over a wide range, and a suitable range includes from about 20 to 0.2 volumes of organic diluent per volume of olefinic hydrocarbon reactant, preferably from about 5 to 1 volumes of organic diluent per volume of olefinic hydrocarbon reactant. Similarly, the broad range for the amount of aqueous phase is from 20 to 0.2 volumes per volume of olefinic hydrocarbon reactant and preferably from 5 to 1 volumes per volume of olefinic hydrocarbon reactant.

It is worth pointing out some predictions relating to the expected effects of the volume of aqueous phase on the oxidation reaction of the instant invention. First, if the aqueous phase volume becomes too small, the concentration of the catalyst components in the aqueous phase can cause a decrease in the solubility of the olefinic hydrocarbon reactant in the aqueous phase, thus greatly slowing down the reaction rate wherein the olefinic hydrocarbon reactant is oxidized to the desired carbonyl compound. Secondly, if the aqueous phase becomes too large, the concentration of catalyst components can be so dilute that the reaction with the olefinic hydrocarbon can also be greatly slowed. However, it can be seen that a judicious choice of the optimum amount of the aqueous phase for high conversion levels of the olefinic hydrocarbon reactant can readily be determined by a few well-chosen experiments.

At present, it is believed that the primary function of the organic phase in the reaction system of the instant invention is to greatly increase the selectivity to the desired carbonyl compound by effectively removing the carbonyl compound product from the locus of the oxidation reaction thereby preventing side reactions such as isomerization and/or further oxidation of the carbonyl compound. However, this explanation is to be treated merely as one possible theory of the mode of action of the organic phase in the reaction and applicants should not be bound to same.

III. Oxygen

As indicated previously, the reaction of the instant invention is an oxidation reaction whereby an olefinic reactant is converted to a carbonyl compound in the presence of a catalyst and diluent system described above. Thus, the reaction of the instant invention is carried out in the presence of free oxygen. The oxygen may be supplied to the reaction mixture essentially as pure oxygen or in admixture with other gases which are essentially inert to the reaction conditions. Air can be utilized as a source of oxygen for the oxidation reaction of this invention.

As is generally true for most oxidation reactions, the reaction of the instant invention can be exothermic and thus some care should be exercised in controlling the amount of oxygen present in the reaction system. For this reason, and also to improve control of the temperature of the reaction, it is preferred to add oxygen or the gaseous mixture containing oxygen to the reaction zone incrementally so that explosive oxygen concentrations do not develop. The pressure of oxygen utilized for the instant invention can be from about 2 up to 250 psig and, preferably, from about 10 to 100 psig above the autogenous pressure at the temperature utilized.

IV. Olefinic Hydrocarbon Reactant

The olefinic hydrocarbon reactant which is oxidized according to the process of the instant invention can be selected from the groups consisting of acyclic olefinic compounds containing from 2–20 carbon atoms per molecule and having 1, 2, or 3 olefinic carbon-carbon double bonds per molecule and cyclic olefinic compounds containing from 5–20 carbon atoms per molecule and having 1, 2, or 3 olefinic carbon-carbon double bonds per molecule. Within the limitations described above, suitable olefinic hydrocarbon reactants can be represented by the general formula RCH=CHR' wherein R and R' are selected from the group consisting of hydrogen, alkyl, alkenyl, alkadienyl, cycloalkyl, cycloalkenyl, and cycloalkadienyl radicals and wherein R can be the same or different from R' and wherein R and R' taken together can form an alkylene or alkenylene or alkadienylene radical thus forming a cyclic system. The term "olefinic carbon-carbon double bond" as used herein is not meant to include those carbon-carbon double bonds which are part of an aromatic carbocyclic system of alternating single and double bonds.

Examples of suitable monoolefinic compounds are ethylene, propylene, 1-butene, 2-butene, 1-pentene, 2-pentene, 1-hexene, 2-hexene, 1-octene, 1-decene, 1-dodecene, 1-hexadecene, 1-octadecene, 1-eicosene, vinyl cyclohexane, cyclopentene, cyclohexene, cycloheptene, cyclooctene, cyclododecene, 3,3-dimethyl-1-butene, and the like.

Examples of suitable diolefinic compounds are 1,3-butadiene, 1,3-pentadiene, 1,5-hexadiene, 4-vinylcyclohexene, 1,5-cyclooctadiene, 1,9-decadiene, 1,7-octadiene, 1,3-cycloheptadiene, and the like.

Suitable triolefinic compounds include 1,5,9-cyclododecatriene, cycloheptatriene, 1,6-diphenyl-1,3,5-hexatriene, and the like.

While the double bond unsaturation can be internal or non-terminal, it is preferred that at least one olefinic carbon-carbon double bond be in the terminal position. That is, the preferred olefinic reactant has at least one terminal olefinic or vinyl group. Mixtures of olefinic reactants can be employed.

V. Reaction Conditions

The particular temperature employed may be dependent somewhat on the olefinic hydrocarbon reactant. For example, at relatively high temperatures, a lower molecular weight olefinic hydrocarbon reactant may tend to be very insoluble in the aqueous phase of the two-phase system of the instant invention, thus causing a reduced conversion of the olefinic hydrocarbon reactant. On the other hand, a higher molecular weight olefinic reactant may be able to tolerate a higher reaction temperature and still maintain a reasonable degree of solubility in the aqueous phase and thus achieve a good degree of conversion at the higher temperature. The temperature utilized in the instant invention is broadly from about 20° to 200° C. and preferably from about 60° to 150° C. Most preferably it lies between about 70° and 100° C.

The time employed for the reaction according to the instant invention can vary over a wide range and will, to some extent, depend on the desired degree of conversion of the olefinic hydrocarbon reactant. Generally, a time period such as from 30 minutes to 8 hours will be employed in the instant invention, preferably 1 to 3 hours.

Because the oxidation reaction according to the instant invention is carried out in the presence of a diluent system comprising at least two liquid phases, it is expected that good stirring will be beneficial. Conventional means of achieving good agitation and contact between the liquid phases can be employed.

The charge order of the reaction components and catalyst components is not critical in the process of the instant invention. However, the presence of oxygen in the reaction mixture prior to heating of the mixture to the desired reaction temperature appears to promote higher selectivity to the desired carbonyl compound.

The process of the instant invention can be carried out in either a batch or continuous process.

Reaction vessels and conduits utilized in the process of the instant invention should, of course, be able to withstand the oxidizing conditions which are present. For this reason, glass-lined, tantalum, titanium or Hastelloy C-clad vessels and conduits are recommended for use in the process of this invention.

VI. Reaction Mixture Workup

A variety of methods can be utilized to recover the products, unreacted olefinic hydrocarbon starting materials, and the catalyst in the aqueous phase in the instant invention. For example, the entire reaction mixture can be subjected to a fractional distillation to separate the components into various fractions or portions. The bottoms from said distillation can be recycled to the reaction zone as that portion contains essentially all of the catalyst system for the reaction.

Another method of treating the reaction mixture is to contact the entire mixture with a lower alkane such as n-pentane, then separate the aqueous phase from the organic phase, with subsequent fractional distillation of the organic phase to recover the products and any unreacted olefinic hydrocarbon reactants. The aqueous phase can be recycled to the reaction zone as described above, since it contains essentially all of the catalyst components.

Another method of reaction mixture workup involves admixture of the reaction mixture with a saturated aqueous sodium chloride solution followed by extraction of the mixture into diethyl ether. The ether extract can then be distilled or treated in such a manner as to remove the ether leaving the organic residue containing the product and any unreacted olefinic hydrocarbon reactant. Said residue can then be subjected to fractional distillation procedures to recover the various components.

VII. Product Utility

As indicated earlier, the reaction of the instant invention provides a process for the conversion of olefinic hydrocarbon reactants to carbonyl compounds. Said carbonyl compounds are ketones, except for the case of ethylene oxidation which yields acetaldehyde. If the olefinic hydrocarbon reactant contains two carbon-carbon double bonds, the product can be an unsaturated monoketone or diketone. Furthermore, the unsaturated monoketone can be recycled to the reaction zone for conversion to the diketone. Similarly a triolefinic reactant can be converted to intermediates such as unsaturated mono- or diketones and ultimately to a triketone. Ketones from the olefinic hydrocarbon reactants described in part IV above have generally well-known utilities. For example, they can be utilized as solvents (methyl ethyl ketone) or as intermediates in the synthesis of other chemical compounds (pinacolone).

VIII. Examples

In all of the runs that are described in the following examples, the reaction vessel utilized was either a 300 cc Hastelloy C Magnedrive stirred tank reactor sold by Autoclave Engineers or a 500 mL Fischer-Porter compatability aerosol bottle. The autoclave was heated by an electric heater and controlled by a Thermoelectric 400 temperature controller. The Fischer-Porter bottles were fitted with pressure gauges, vent and chargelines through which oxygen could be added continuously or incrementally. The oxygen line to the reaction vessel was fitted with the appropriate check valves and flame arrestor. The bottle was heated in an ethylene glycol bath, and monitored on an Acromag by a thermocouple placed in the glycol bath. The bottle contents were stirred by a magnetic stirrer.

For autoclave runs, the reactor was charged with the catalyst system, the diluents, and then sealed. Thirty psig oxygen pressure was introduced to pressure test the reactor, then vented. The olefinic reactant was then charged, while autoclave stirring was begun to aid olefin dissolution in the organic diluent. Thirty psig oxygen pressure was again introduced and the autoclave heated to the desired reaction temperature before the oxygen pressure was adjusted to the desired operating pressure. The reaction was allowed to take-up oxygen on demand for the duration of the reaction in order to maintain the desired pressure. For runs carried out in the Fischer-Porter bottles, the catalyst, diluents, and olefinic reactant were charged. The bottle was assembled with the proper fittings, placed in the ethylene glycol bath, and stirring begun. An initial pressure of 30 psig oxygen was introduced, the reaction mixture heated to the desired reaction temperature, then oxygen pressure raised to the desired reaction value. As above, the system was allowed to take-up oxygen on demand to maintain the desired operating pressure throughout the reaction.

After the desired reaction time had elapsed the reaction was cooled to room temperature before excess oxygen was vented. The combined organic and aqueous phases were subjected to conventional fractional distillation to recover volatile materials (starting material, products and by-products). After distillation, the residual materials were phase separated, decane solvent being recycled to the reactor while the aqueous phase was evaporated to dryness, the residue redissolved in deionized water, $H_2SO_4$ added to adjust pH to 1.9 and the resulting solution was then recycled to the reactor. All samples were analyzed by gas-liquid phase chromatography.

All temperatures are degrees C unless specified otherwise.

EXAMPLE I

Preparation of the Phospho-6-molybdo-6-vanadic acid 45.5 g $Na_3PO_4.12H_2O$ (0.12 mol), 103.6 g $MoO_3$ (0.72 mol), 42.0 g $V_2O_5$ (0.23 mol) and 22.4 g $Na_2CO_3.10H_2O$ (0.08 mol) were dissolved in 600 mL $H_2O$. The solution was heated to boiling and stirred vigorously for 40 minutes. The solution gradually turned an intense brownish-red. The solution volume was reduced to 150 mL by evaporation, then allowed to cool to room temperature. The pH of the solution was adjusted to 1.00 with concentrated sulfuric acid, the solution was then filtered and set aside for use as a component in the inventive oxidation process.

EXAMPLE II

Two control runs were carried out in which 2-butene was oxidized to methyl ethyl ketone (MEK) in the absence of organic diluent and surfactant component. Both runs were carried out in 300 cc Hastelloy C autoclaves following the general procedure set forth above. One hundred mL of water and reagents in the amounts specified in Table I were treated for 2 hours at 80° C. and 100 psig.

TABLE I

| Run # | $PdCl_2$, mol | Heteropoly- acid, mol | Butene Charged, mol | Butene Conversion, mol % | Selectivity to MEK, mol % |
|---|---|---|---|---|---|
| 1 | .01 | .05 | 0.48 | 17.7 | 77.5 |
| 2 | .005 | .025 | 0.86 | 0.04 | 100 |

The results of these runs demonstrate the poor performance of the palladium-heteropolyacid catalyst system at 80° and 100 psig when carried out in aqueous phase only.

EXAMPLE III

A control run was carried out in which 2-butene was oxidized to MEK utilizing the inventive catalyst system in a two-phase medium in the absence of the surfactant component. The reaction was carried out in a 500 mL Fischer-Porter bottle according to the general procedure set forth above. One hundred mL water and 100 g (137 mL) decane containing 0.01 mol $PdCl_2$, 0.05 mol heteropolyacid, and 0.46 mol 2-butene were reacted for 2 hours at 80° C. and 100 psig. Analysis of the final product revealed a 2-butene conversion of only 2.9% with a selectivity to MEK of 99.6%.

The results of this run demonstrate the poor performance of the palladium/heteropolyacid catalyst system in two-phase medium in the absence of surfactant component.

EXAMPLE IV

The reaction of 2-butene was carried out in the presence of 75 mL water, 75 g (103 mL) decane, 0.01 mol $PdCl_2$, 0.04 mol heteropolyacid and 1.4 g (0.004 mol) cetyltrimethylammonium bromide (CTMAB) as surfactant component. 0.52 mol 2-butene were reacted in a 500 mL Fischer-Porter bottle according to the general procedure set forth above at 80° C. and 80 psig for 3 hours. Analysis of the final product revealed a 2-butene conversion of 55.4% with selectivity to MEK of 84.2%.

The results of this run demonstrate the operability of this invention in a two-phase medium which comprises $PdCl_2$, a heteropolyacid and surfactant component.

EXAMPLE V

A series of 2-butene oxidations were carried out utilizing the same catalyst charge for numerous recycles, occasionally recharging catalyst components (as noted in Table II below) to compensate for handling losses. All reactions were carried out using a 500 mL Fischer-Porter bottle containing 100 mL water, 100 g (137 mL) decane, and reagents in the amounts tabulated in Table II. Reactions were carried out for 2 hours at 80° and 100 psig according to the general procedure set forth above.

TABLE II

| Run # | PdCl$_2$, mol | HPA*, mol | CTMAB, mol | Butene Charged, mol | Butene Conversion, mol % | Selectivity to MEK, mol % |
|---|---|---|---|---|---|---|
| 1 | 0.01 | 0.05 | 0.004 | 0.47 | 64.2 | 84.5 |
| 2 | +.0001 | " | +.00003 | 0.46 | 56.4 | 87.7 |
| 3 | " | " | " | 0.45 | 80.2 | 87.5 |
| 4 | " | " | " | 0.48 | 68.0 | 90.1 |
| 5 | +.0001 | " | +.00003 | 0.49 | 65.5 | 90.2 |
| 6 | " | " | " | 0.48 | 69.7 | 89.9 |
| 7 | +.0001 | " | +.00003 | 0.45 | 82.3 | 89.0 |
| 8 | " | " | " | 0.44 | 78.7 | 89.6 |

*Heteropolyacid

These runs demonstrate the operability of the process of this invention for the oxidation of 2-butene to methyl ethyl ketone, and the continued excellent performance of the inventive oxidation system through numerous recycles.

EXAMPLE VI

A control run was carried out in which 1-butene was oxidized to methyl ethyl ketone utilizing the inventive catalyst system in a two-phase medium in the absence of the surfactant component. The reaction was carried out in a 500 mL Fischer-Porter bottle according to the general procedure set forth above. One hundred mL water and 100 g (137 mL) decane containing 0.01 mol PdCl$_2$, 0.05 mol heteropolyacid, and 0.45 mol 1-butene were reacted for 2 hrs. at 80° and 100 psig. Analysis of the final product revealed a 1-butene conversion of only 3.3% with a selectivity to MEK of 90.5%.

The results of this run demonstrate the poor performance of the palladium/heteropolyacid catalyst system in two-phase medium in the absence of the surfactant component.

EXAMPLE VII

A series of 1-butene oxidations were carried out utilizing the same catalyst charge for numerous recycles, with intermittent replenishing of catalyst components (as noted in Table III, below) to compensate for handling losses associated with catalyst recycle. All reactions were carried out using a 500 mL Fischer-Porter bottle containing 100 mL water, 100 g (137 mL) decane and reagents in the amounts tabulated in Table III. Reactions were carried out for 2 hours at 80° and 100 psig according to the general procedure set forth above.

TABLE III

| Run # | PdCl$_2$, mol | HPA*, mol | CTMAB, mol | Butene Charged, mol | Butene Conversion, mol % | Selectivity to MEK, mol % |
|---|---|---|---|---|---|---|
| 1 | 0.01 | 0.05 | 0.004 | 0.45 | 56.0 | 92.7 |
| 2 | " | " | " | 0.45 | 65.0 | 92.8 |
| 3 | +0.0001 | " | +.00003 | 0.46 | 70.5 | 91.4 |
| 4 | " | " | " | 0.43 | 80.2 | 90.5 |
| 5 | +0.0001 | " | +.00003 | 0.46 | 77.6 | 92.3 |
| 6 | " | " | " | 0.46 | 80.5 | 90.0 |
| 7 | +0.0001 | " | +.00003 | 0.46 | 79.3 | 91.9 |
| 8 | " | " | " | 0.45 | 80.0 | 91.2 |
| 9 | +0.0001 | " | +.00003 | 0.48 | 88.4 | 90.6 |
| 10 | " | " | " | 0.44 | 89.0 | 90.0 |
| 11 | +0.0001 | " | +.00003 | 0.46 | 89.8 | 93.0 |
| 12 | " | " | " | 0.45 | 88.0 | 93.6 |
| 13 | " | " | " | 0.44 | 92.6 | 92.0 |
| 14 | " | " | " | 0.45 | 75.3 | 95.5 |
| 15 | " | " | " | 0.45 | 85.7 | 93.7 |

*Heteropolyacid

These runs demonstrate the operability of the process of this invention for the oxidation of 1-butene to methyl ethyl ketone. In addition, the inventive oxidation system is shown to perform well through numerous recycles.

EXAMPLE VIII

A series of 1-butene oxidations were carried out in the 300 cc Hastelloy C autoclave. All reactions were carried out at 80° and 100 psig for 2 hours according to the general procedure set forth above. The charge consisted of 60 mL water, 60 g (82 mL) decane, and reagents in the amounts tabulated.

TABLE IV

| Run # | PdCl$_2$, mol | HPA*, mol | CTMAB, mol | Butene Charged, mol | Butene Conversion, mol % | Selectivity to MEK, mol % |
|---|---|---|---|---|---|---|
| 1 | .006 | 0.31 | .002 | 0.25 | 89.8 | 82.4 |
| 2 | " | " | " | 0.29 | 87.9 | 85.7 |
| 3 | " | " | " | 0.29 | 90.8 | 85.6 |
| 4 | " | " | " | 0.30 | 87.0 | 86.7 |
| 5 | " | " | " | 0.41 | 66.3 | 91.2 |

TABLE IV-continued

| Run # | PdCl$_2$, mol | HPA*, mol | CTMAB, mol | Butene Charged, mol | Butene Conversion, mol % | Selectivity to MEK, mol % |
|---|---|---|---|---|---|---|
| 6 | " | " | " | 0.29 | 80.0 | 89.0 |

*Heteropolyacid

These runs demonstrate the increased level of conversion attainable with more efficient stirring (magnedrive vs. magnetic stir bar) when runs 1–6 of Tables III and IV are compared.

EXAMPLE IX

A series of 1-butene oxidations were carried out utilizing the same catalyst charge for numerous recycles, with intermittent replenishing of catalyst components (as noted in Table V, below) to compensate for handling losses associated with catalyst recycle. All reactions were carried out in a 500 mL Fischer-Porter bottle containing 100 mL water, 100 g (137 mL) decane, and reagents in the amounts tabulated in Table V. Reactions were carried out for 1 hour at 80° and 100 psig.

TABLE V

| Run # | PdCl$_2$, mol | HPA*, mol | CTMAB, mol | Butene Charged, mol | Butene Conversion, mol % | Selectivity to MEK, mol % |
|---|---|---|---|---|---|---|
| 1 | 0.01 | 0.05 | 0.004 | 0.35 | 47.9 | 92.7 |
| 2 | " | " | " | 0.35 | 41.4 | 94.5 |
| 3 | +.001 | " | +.0003 | 0.37 | 65.7 | 91.4 |
| 4 | " | " | " | 0.37 | 55.8 | 91.1 |
| 5 | +.001 | " | +.0003 | 0.38 | 62.7 | 91.9 |
| 6 | " | " | " | 0.35 | 67.5 | 92.2 |
| 7 | +.001 | " | +.0003 | 0.34 | 66.6 | 93.3 |
| 8 | " | " | " | 0.36 | 73.6 | 91.7 |
| 9 | +.001 | " | +.0003 | 0.38 | 75.3 | 93.3 |
| 10 | " | " | " | 0.37 | 69.5 | 92.8 |
| 11 | " | " | " | 0.38 | 67.9 | 93.3 |
| 12 | " | " | " | 0.37 | 50.5 | 96.4 |
| 13 | " | " | " | 0.38 | 68.3 | 94.5 |
| 14 | " | " | " | 0.38 | 62.2 | 95.9 |

*Heteropolyacid

These runs demonstrate the operability of the present invention for the conversion of 1-butene to MEK with substantial conversion in only one hour reaction time.

EXAMPLE X

Several runs were carried out to determine the corrosive nature of the inventive catalyst system. Metal coupons were placed in 500 mL Fischer-Porter bottles and subjected to typical reaction conditions. Hastelloy C and stainless steel (316) coupons were treated for 2 hours at 85° and 100 psig O$_2$ in the presence of 0.005 mol PdCl$_2$, 0.025 mol heteropolyacid, 0.002 mol CTMAB, and 0.11 mol H$_3$BO$_3$ in 50 mL water. Coupons were removed from the reactor, washed, dried and weighed. There was no measurable weight loss by the Hastelloy C coupon, and only 0.0001 g weight loss by the stainless steel coupon.

For comparison, titanium, Hastelloy B and Hastelloy C coupons were similarly treated under typical modified Wacker oxidation conditions. Thus, coupons were subjected to 2 hours at 100° C. and 100 psig O$_2$ in a Fischer-Porter bottle containing 0.015 mol PdCl$_2$, 0.095 mol CuCl$_2$, 0.007 mol cetyltrimethylammonium chloride, and 0.38 mol H$_3$BO$_3$ in 150 mL water. Coupons were removed from the reactor, washed, dried and weighed. The titanium coupon showed no weight loss, while the Hastelloy B coupon lost 1.5196 g (or 17% of original coupon weight) and Hastelloy C coupon lost 0.0059 g (or 0.04% of original coupon weight).

These runs demonstrate the substantially reduced corrosive nature of the inventive catalyst system.

EXAMPLE XI

Oxidation of 2-butene was carried out with palladium nitrate as the palladium component, heteropolyacid as prepared in Example I, 40 mL water, 50 g (68 mL) decane, and cetyltrimethylammonium bromide as surfactant component. Reactions were carried out in a 250 mL Fischer-Porter aerosol compatibility bottle equipped in an analogous manner to the 500 mL Fischer-Porter bottle described earlier. Reactions were carried out for 3 hours at 80° C. and 80 psig according to the general procedure set forth above. Catalyst was regenerated between runs by treating the aqueous phase in the same 250 mL Fischer-Porter bottle for 5 hours at 105°–110° C. and 100 psig oxygen pressure. Catalyst charge and results are tabulated in Table VI.

TABLE VI

| Run # | Pd(NO$_3$)$_2$, mol | HPA*, mol | CTMAB, mol | Butene Charged, mol | Butene Conversion, mol % | Selectivity to MEK, mol % |
|---|---|---|---|---|---|---|
| 1 | 0.005 | 0.02 | 0.002 | 0.24 | 27.4 | 91.6 |
| 2 | " | " | " | 0.28 | 16.1 | 61.2 |

*Heteropolyacid

These runs demonstrate the operability of the process of this invention for the oxidation of 2-butene to MEK with a chloride-free palladium salt.

EXAMPLE XII

Oxidations of 1- and 2-butene were carried out with palladium sulfate as the palladium component. All reactions were carried out in a 500 mL Fischer-Porter bottle to which was charged 100 mL water, 100 g (137 mL) decane, and catalyst components as specified in Table VII. Reactions were carried out at 80° and 100 psig oxygen for 3 hours according to the general procedure set forth above.

TABLE VII

| Run # | PdSO$_4$, mol | HPA*, mol | CTMAB, mol | Butene Charged, mol | Butene Conversion, mol % | Selectivity to MEK, mol % |
|---|---|---|---|---|---|---|
| 1-Butene | | | | | | |
| 1 | 0.01 | 0.05 | 0.004 | 0.43 | 45.5 | 92.8 |
| 2 | " | " | " | 0.43 | 43.7 | 91.1 |
| 3 | +0.002 | " | " | 0.46 | 47.6 | 91.0 |
| 4 | " | " | " | 0.45 | 44.4 | 93.6 |
| 5 | " | " | " | 0.46 | 49.5 | 92.7 |
| 2-Butene** | | | | | | |
| 1 | 0.01 | 0.05 | 0.004 | 0.45 | 27.4 | 90.2 |
| 2 | " | " | " | 0.43 | 37.8 | 90.1 |
| 3 | " | " | " | 0.46 | 31.8 | 88.6 |
| 4 | " | " | " | 0.45 | 43.3 | 85.7 |
| 5 | " | " | " | 0.45 | 41.5 | 84.5 |

*Heteropolyacid
**All 2-butene runs include 0.25 mol boric acid.

These runs demonstrate the operability of the process of this invention for the oxidation of 1- or 2-butene to MEK with a chloride-free palladium salt.

EXAMPLE XIII

The oxidation of 1-butene was carried out with a mixture of palladium chloride/palladium sulfate as the palladium component. All reactions were carried out in a 500 mL Fischer-Porter bottle to which was charged 100 mL water, 100 g (137 mL) decane, and catalyst components as specified in Table VIII. Reactions were carried out at 80° and 100 psig oxygen for 2 hours according to the general procedure set forth above. In all runs, 0.05 mol of heteropolyacid and 0.004 mol of CTMAB were utilized.

TABLE VIII

| Run # | Pd charge, mol Total | as PdCl$_2$ | as PdSO$_4$ | Butene Charged, mol | Butene Conversion, mol % | Selectivity to MEK, mol % |
|---|---|---|---|---|---|---|
| 1 | 0.01 | .0025 | .0078 | 0.40 | 59.6 | 89.8 |
| 2 | " | " | " | 0.44 | 54.5 | 92.4 |
| 3 | " | " | " | 0.43 | 56.4 | 91.3 |
| 4 | " | " | " | 0.43 | 60.8 | 89.4 |
| 5 | " | " | " | 0.45 | 65.8 | 87.1 |
| 6 | " | " | " | 0.41 | 75.6 | 92.7 |
| 7 | " | " | " | 0.41 | 78.7 | 88.9 |
| 8 | " | " | " | 0.48 | 71.1 | 90.1 |
| 9 | " | " | " | 0.43 | 76.6 | 92.0 |
| 10 | " | " | " | 0.48 | 73.9 | 94.2 |
| 11 | " | " | " | 0.46 | 88.7 | 91.4 |
| 12 | " | " | " | 0.48 | 85.8 | 91.6 |

These runs demonstrate the operability of the process of this invention for the oxidation of 1-butene to MEK utilizing a mixture of palladium compounds. The chloride content of the catalyst composition is reduced by ¼ with oxidation activity comparable to that demonstrated in Example VII above.

EXAMPLE XIV

The oxidation of neohexene (3,3-dimethyl-1-butene) was carried out in a 300 cc titanium Autoclave Engineers magnedrive stirred tank reactor. The reactor was charged with 50 mL water, 50 g (68 mL) decane, 0.025 mol heteropolyacid, 0.002 mol cetyltrimethylammonium bromide, 0.24 mol neohexene, and palladium chloride as indicated in Table IX. Reactions were carried out according to the general procedure set forth above, under conditions specified in Table IX.

TABLE IX

| Run # | PdCl$_2$, mol | Reaction Conditions Temperature, °C. | Pressure, psig | Time, hr. | Neohexene conversion, mol % | Pinacolone selectivity, mol % |
|---|---|---|---|---|---|---|
| 1 | 0.01 | 120 | 150 | 3 | 36.5 | 98.1 |
| 2 | 0.005 | 150 | 250 | 4 | 91.5 | 80.0 |

These runs demonstrate that the process of this invention can be used for the oxidation of neohexene with excellent selectivities to pinacolone.

EXAMPLE XV

The oxidation of 3-methyl-1-butene was carried out in a 300 cc titanium Autoclave Engineers magnedrive stirred tank reactor. The reactor was charged with 50 mL water, 50 g (68 mL) decane, 0.01 mol palladium chloride, 0.025 mol heteropolyacid, 0.004 mol cetyltrimethylammonium bromide, and 0.29 mol 3-methyl-1-butene. Reaction was carried out for 2 hours, at 120° C. and 150 psig oxygen pressure according to the general procedure set forth above. A 22.1 mol % conversion of 3-methyl-1-butene was obtained with 37.1% selectivity to methyl isopropyl ketone.

This example demonstrates the operability of the process of this invention for the oxidation of 3-methyl-1-butene to methyl isopropyl ketone.

Reasonable variations, such as those which would occur to a skilled artisan, may be made in the invention without departing from the scope thereof.

We claim:

1. Composition useful for the catalytic oxidation of olefins to carbonyl compounds comprising:
   (a) one or more palladium components;
   (b) one or more heteropolyacid components conforming to the general formula $$H_m[X_xMo_aV_bM_yO_z]$$

in which
X is B, Si, Ge, P, As, Se, Te or I;
M is W, Nb, Ta or Re;
m, a, b and z are integers;
x is zero or an integer;
and y is zero or an integer such that $$6 \leq (y+a+b)/z \leq 12$$

and $$m + Nx + 6a + 5b + N'y \leq 2z;$$

in which each of N and N' is the number of the group of the periodic table to which X and M respectively belong;
(c) one or more surfactants selected from the group consisting of: quaternary ammonium salts, alkali metal alkyl sulfates, alkali metal salts of alkanoic acids, alkali metal salts of alkaryl sulfonic acids, and 1-alkyl pyridinium salts; and
(d) two or more liquid phases comprising an aqueous phase and an organic phase.

2. The composition of claim 1 wherein (a) is selected from palladium metal, palladium compounds and mixtures thereof.

3. The composition of claim 1 wherein (b) is selected from heteropolyacids having redox potentials in excess of 0.5 volts.

4. The composition of claim 1 wherein (a) is palladium chloride and (b) is $H_9[PMo_6V_6O_{40}]$.

5. The composition of claim 4 wherein (c) is cetyltrimethylammonium bromide.

6. The composition of claim 5 wherein (d) contains water and decane.

7. The composition of claim 1 wherein the molar ratio of olefinic reactant to (a) is from about 5:1 to about 1000:1.

8. The composition of claim 1 wherein the molar ratio of (b) to (a) is not more than about 50:1.

9. The composition of claim 8 wherein the molar ratio of (c) to (a) is about 0.01:1 to about 10:1.

* * * * *